United States Patent [19]

Greindl et al.

[11] Patent Number: 6,147,258
[45] Date of Patent: Nov. 14, 2000

[54] PREPARATION OF SUBSTITUTED GUANIDINE DERIVATIVES

[75] Inventors: Thomas Greindl, Bad Dürkheim; Günter Scherr, Ludwigshafen; Rolf Schneider, Mannheim; Klaus Mundinger, Limburgerhof, all of Germany

[73] Assignee: BASF Aktiengesellschaft, Ludwigshafen, Germany

[21] Appl. No.: 09/176,904

[22] Filed: Oct. 22, 1998

[30] Foreign Application Priority Data

Nov. 4, 1997 [DE] Germany .......................... 197 48 697

[51] Int. Cl.$^7$ .................................................. C07C 279/20
[52] U.S. Cl. ........................... 562/560; 558/435; 564/80; 564/193; 564/230; 564/232; 564/240; 564/241; 564/242
[58] Field of Search ............................. 562/560; 564/230, 564/232, 240, 241, 242, 193, 80; 558/435

[56] References Cited

U.S. PATENT DOCUMENTS

| | | | |
|---|---|---|---|
| 2,425,341 | 8/1947 | Paden et al. | 564/240 |
| 5,719,319 | 2/1998 | Weiss et al. | 562/560 |

FOREIGN PATENT DOCUMENTS

| | | |
|---|---|---|
| 0 754 679 | 1/1997 | European Pat. Off. . |
| 964 590 | 5/1957 | Germany . |

OTHER PUBLICATIONS

P.E. Gagnon, et al., Can. J. Chem., Vol. 36, pp. 737–743, "Alkylguanidine Nitrates and Alkylnitroguanidines," 1958.

*Primary Examiner*—Shailendra Kumar
*Attorney, Agent, or Firm*—Oblon, Spivak, McClelland, Maier & Neustadt, P.C.

[57] ABSTRACT

Substituted guanidine derivatives of the formula I

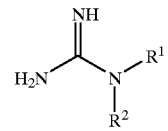

are prepared by reacting calcium cyanamide with a primary or secondary amino carboxylic acid or a primary or secondary amino sulfonic acid or their derivatives of the formula II

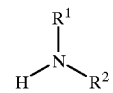

where the substituents $R^1$ and $R^2$ have the meanings explained in the description.

15 Claims, No Drawings

PREPARATION OF SUBSTITUTED GUANIDINE DERIVATIVES

The present invention relates to an improved process for preparing substituted guanidinium compounds by reacting calcium cyanamide with a primary or secondary amino carboxylic acid or a primary or secondary amino sulfonic acid or derivatives thereof.

Substituted guanidinium compounds are widespread in nature. Examples of important representatives of this class of substances are amino acids such as arginine and creatine. In addition, substituted guanidine compounds are known as sterically hindered bases, as biocides and as complex ligands. However, the industrial utilizability of most of the compounds of this type is greatly restricted owing to the high production costs thereof.

One example of a biologically active guanidine derivative is creatine which, as the cell's energy carrier, is employed as dietary supplement in the food and drugs sector.

The synthesis of guanidinium salts from cyanamide is known and is described, for example, in U.S. Pat. No. 2,425,341, where aqueous cyanamide solutions are reacted with aqueous solutions of the amines at >80° C. and at pH >8.

The preparation of creatine is described, for example, in EP-A-0 754 679 and the further literature quoted therein, the maximum yields being only 70%.

One disadvantage of the abovementioned syntheses of guanidinium compounds is the use of aqueous solutions of pure cyanamide. These solutions are very costly and, owing to the instability of cyanamide, generally not widely available.

The industrial preparation of pure cyanamide or aqueous solutions thereof starts from nitrolime. However, production is complicated because, owing to the great instability of cyanamide, special precautions must be taken during preparation and storage. The preparation is described, for example, in D.R.P. 267514 and D.R.P. 648542.

It is an object of the present invention to provide a low-cost and easily implemented process for preparing substituted guanidines based on widely available starting materials and not having the abovementioned disadvantages.

We have found that this object is achieved by a process for preparing substituted guanidine derivatives of the formula I,

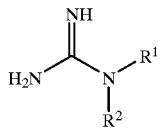

which comprises reacting calcium cyanamide with a primary or secondary amino carboxylic acid or a primary or secondary amino sulfonic acid or derivatives thereof, of the formula II

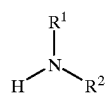

where the substituents $R^1$ and $R^2$ have, independently of one another, the following meanings:

$R^1$ H, $C_1$–$C_{20}$-alkyl;
$R^2$ —($C_1$–$C_{20}$-alkylene)—COOR$^3$, —($C_1$–$C_{20}$-alkylene)—CONR$^4$R$^5$, —($C_1$–$C_{20}$-alkylene)—CN, —($C_1$–$C_{20}$-alkylene)—SO$_2$R$^6$;
$R^3$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, N(R$^1$)$_4$;
$R^4$ and $R^5$ independently of one another H, $C_1$–$C_{20}$-alkyl, $C_2$–$C_{10}$-alkenyl, $C_3$–$C_8$-cycloalkyl, $C_6$–$C_{18}$-aryl;
$R^6$ OR$^7$, N(R$^8$)$_2$;
$R^7$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, N(R$^1$)$_4$;
$R^8$ H, $C_1$–$C_{20}$-alkyl, $C_2$–$C_{10}$-alkenyl, $C_3$–$C_8$-cycloalkyl, $C_6$–$C_{18}$-aryl.

The novel process thus complies in particular with commercial limiting conditions such as low costs of starting materials, easy industrial implementation, improved yields and adequate purity of the product.

Suitable in principle for the reaction with calcium cyanamide are all the claimed amino carboxylic acids and amino sulfonic acids and derivatives thereof of the formula II.

Alkyl radicals which may be mentioned for $R^1$, $R^3$ to $R^5$ and $R^7$ to $R^8$ are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals which may be mentioned for $R^3$ to $R^5$ and for $R^7$ and $R^8$ are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Alkylene radicals which may be mentioned for $R^2$ are branched or unbranched $C_1$–$C_{20}$-alkylene chains, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene, n-nonylene, n-decylene, n-undecylene, n-dodecylene, n-tridecylene, n-tetradecylene, n-pentadecylene, n-hexadecylene, n-heptadecylene, n-octadecylene, n-nonadecylene or n-eicosylene.

The 1- to 20-membered alkylene chains may be substituted by the following radicals:

$C_1$–$C_6$-alkyl, for example methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl;

mercaptomethyl, 1-aminobutyl, 1-carboxyethyl;

arylalkyl, for example benzyl, p-hydroxybenzyl, indolylmethyl.

Cycloalkyl radicals which may be mentioned for $R^3$ to $R^5$ and for $R^7$ and $R^8$ are preferably branched or unbranched $C_3$–$C_8$-cycloalkyl radicals such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl or cyclooctyl.

The cycloalkyl radicals may be substituted by one or more, eg. 1 to 3, radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms, such as sulfur, nitrogen, whose free valencies can be saturated by hydrogen or $C_1$–$C_4$-alkyl, or oxygen, in the ring.

Suitable alkoxy radicals for $R^6$ are those having 1 to 20 carbon atoms, preferably having 1 to 12 carbon atoms, particularly preferably 1 to 8 carbon atoms.

Examples which may be mentioned are:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Suitable and preferred mono- or disubstituted amino radicals for $R^6$ are those containing alkyl radicals having 1 to 20, preferably 1 to 12, carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Suitable tetraalkylammonium radicals for $R^3$ and $R^7$ are those containing alkyl radicals having 1 to 20, preferably 1 to 12, particularly preferably 1 to 6, carbon atoms, such as methyl, n-propyl, isopropyl, 2-methylpropyl, 1,1-dimethylpropyl, 1-methylpropyl, 2,2-dimethylpropyl, 1-methyl-1-ethylpropyl, n-butyl, 3-methylbutyl, n-pentyl and hexyl.

Aryl means aromatic rings or ring systems having 6 to 18 carbon atoms in the ring system, for exmaple phenyl or naphthyl, each of which may be substituted by one or more radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Compounds of the formula II which are preferably used are all the primary and secondary amino carboxylic acids or amino sulfonic acids which are soluble in water or in water-miscible solvents. Particularly preferred representatives include taurine and amino carboxylic acids such as glycine, alanine, valine, proline, leucine, phenylalanine, lysine, methionine, cysteine, aspartic acid, iminodiacetic acid and sarcosine and their esters, amides and nitriles and their salts.

The very particularly preferred compound of the formula II is sarcosine which can be used both as free acid and, in particular, as Na or K salt in the form of a 5 to 60% by weight, preferably 35 to 45% by weight, aqueous solution.

The novel process for preparing substituted guanidine derivatives is particularly distinguished by the possibility of employing in place of the costly pure cyanamide, which is normally commercially available as crystalline pure product or as a solution stabilized at pH 3–6, the very low-cost and widely available nitrolime.

Nitrolime means products which are obtained, for example, by reacting $CaC_2$ with $N_2$ at 800–1100° C. As a rule, they contain 5–98% by weight, preferably 20–95% by weight, particularly preferably 30–90% by weight, of calcium cyanamide. The industrially available gray to black nitrolime contains not only calcium cyanamide but also impurities such as carbon, calcium carbide, CaO and traces of metals, normally in contents <1%. It is, of course, also possible to use pure calcium cyanamide. However, it is particularly advantageous, because more economical, to use technical, not very pure nitrolime. This is preferably employed in the form of a powder with a particle size distribution from 1 to 100 μm. However, it is also possible to employ granulated, extruded or otherwise compacted material, as well as an appropriate suspension in water, alcohols or other water-miscible solvents.

The reaction of calcium cyanamide with ammonia is described in U.S. Pat. No. 2,114,280. In this case, calcium cyanamide is reacted with an excess of ammonia under elevated pressure at >130° C. to give unsubstituted guanidine.

Gagnon et al. in Can. J. Chem. 36 (1958) describe the reaction of calcium cyanamide with primary $C_1$–$C_5$-amine nitrates.

H. Michaud et al. in Chem. Ztg. 112 (1988) 10, 287–294 and F. Baum in Biochem. Z. 26 (1910), 325–332 report that in some cases large amounts of byproducts such as dicyandiamide and urea result on hydrolysis of nitrolime without addition of acid.

To prevent these side reactions it is necessary, on the one hand, to keep the temperature below 40° C., better below 20° C., which necessitates costly cooling and, on the other hand, the pH must be brought into the acidic range by adding acids, in particular carbonic acid.

However, this procedure is time-consuming and, moreover, results in a very dilute cyanamide solution, which must be concentrated by additional distillation.

It is also known that alkaline cyanamide hydrolysis is catalyzed by heavy metal ions, in particular by iron and manganese.

It was therefore all the more surprising that technical calcium cyanamide can be converted in the presence of traces of heavy metals in an alkaline medium into the guanidine derivative in good yields.

Another advantage of the process is the fact that the nitrolime used, which itself undergoes alkaline reaction in water, does not require acidic hydrolysis in a separate step but, surprisingly, can be employed without further pretreatment directly at the desired pH for the reaction with the amine. The pH normally used in this case is in the region of the pK of the amine, ie. in a range from 6 to 14, preferably from 8 to 12, particularly preferably from 9 to 11.

This saves considerable amounts of acid compared with the separate preparation of cyanamide from calcium cyanamide and subsequent conversion to the guanidine, because the novel process is carried out exclusively in alkaline medium.

The synthesis can take place in such a way that nitrolime is metered into a solution of a primary or secondary amine while keeping the pH constant in the abovementioned range. It is possible to meter in a solid or a suspension for this purpose. The reaction in this case is carried out at from 20 to 120° C., in particular from 40 to 80° C.

Nitrolime is added in equal portions over a period of from 0.5 to 10 h, preferably from 1 to 6 h, particularly preferably from 2.5 to 3 h.

The metering is, as a rule, followed by stirring for 0.5 to 10 h, preferably 1 to 3 h.

The molar ratio of calcium cyanamide to primary or secondary amine is in the range from 0.9 to 5.0, preferably from 0.9 to 4.0, in particular from 1.0 to 2.0.

To remove dissolved heavy metal ions, it may be advantageous to employ complexing agents such as phosphates, sulfates, aminopolycarboxylates, for exaple EDTA or aminopolyphosphonates.

To eliminate odoriferous byproducts it is possible also to add oxidizing agents such as $H_2O_2$.

It is possible in this way to improve the purity of the resulting guanidine derivative without any losses of yield.

After the reaction, any precipitated inorganic byproducts can be removed at from 20 to 100° C., preferably 50 to 90° C., by processes known per se, such as filtration or centrifugation.

The required guanidinium derivatives are isolated in a manner known per se. Thus, for example, the required product can be obtained as crystals by cooling the filtered reaction solution to −20 to 60° C., in particular 0 to 40° C. Filtration can, where appropriate, be followed by recrystallization to improve the purity. However, it is also possible to remove the product from the reaction mixture by extraction in order then to isolate it pure by distillation or crystallization.

Another advantage of the novel process is that industrially costly cooling, as required for the preparation of cyanamide, can be dispensed with. Because of the mild temperatures used, the reaction can be carried out under atmospheric pressure, which is particularly simple industrially.

It is particularly surprising that the yields of the novel reaction are comparable with those from the reaction of pure cyanamide, and are therefore higher, based on the calcium cyanamide content, for the overall process of liberation of the cyanamide and reaction to give the guanidinium salt, because of the smaller number of steps.

In addition, it is possible to achieve higher conversions by employing the low-cost nitrolime in excess, which is frequently uneconomical when pure cyanamide is used. The purity of the isolated guanidinium salt is comparable with that of the product prepared from pure cyanamide. This is particularly surprising because the technical starting material is highly impure.

It is possible to use as starting materials not only the calcium salt of cyanamide but also other alkaline earth metal salts.

It is also possible in the case of the primary and secondary amines to employ not only the pure substances but in particular, advantageously, technical products, eg. in place of pure sarcosine a technical sodium salt solution with active substance contents of 5–60%, but preferably 40%, which may also contain water-soluble impurities such as N-methyliminodiacetic acid.

The use of technical products is particularly advisable when no other reactive amines are present and it is particularly economically advantageous because, for example, the purification of the amine is costly and results in large losses.

The pH can be maintained by employing, depending on the initial pH of the base, either acids such as $CO_2$, $SO_2$, HCl, $HNO_3$, $H_2SO_4$, $H_2SO_3$, $H_3PO_3$, $H_3PO_2$ and $H_3PO_4$, and/or bases such as NaOH, KOH, LiOH, $Ca(OH)_2$, $Ba(OH)_2$, $Mg(OH)_2$. Only acids are required if the amines should be present in basic and not in neutralized or partially neutralized form.

Preferred acids are those which are easily available industrially and result together with traces of heavy metals in complexes of low solubility, such as $CO_2$, $H_2SO_4$, $H_3PO_4$. However, it is also possible and preferred to employ mixtures of these and other acids.

The process for preparing substituted guanidinium derivatives is explained in detail in the following examples.

EXAMPLE 1

Reaction of sarcosine sodium salt solution with calcium cyanamide at pH 10 in the presence of sulfuric acid In a 2 l reactor with reflux condenser, paddle stirrer, thermostat and pH-controlled sulfuric acid metering, a total of 14.0 g of 50% strength sulfuric acid was metered into a mixture of 133 g of 40.1% strength aqueous sodium sarcosinate solution and 53 g of water to adjust to a pH of 10. Then, at 60° C., a total of 87.2 g of nitrolime (supplied by Aldrich, granular product, $CaCN_2$ content=84%) were added in portions over the course of 2 h. In order to keep the pH at 10, a total of 403 g of 25% strength sulfuric acid was metered in during the addition period. The temperature was kept at 60° C. by cooling. After the addition was complete, stirring was continued at the stated temperature for 2 h, and the mixture was then heated to 80° C. over the course of 20 min. The resulting greenish suspension was filtered at 80° C., and the black filter cake was washed twice with 250 ml of water at 80° C. The mother liquor and washing water were combined and treated with 2 g of 85% strength $H_3PO_4$. The fine colorless precipitate which formed was filtered off, and the now colorless solution was cooled to 5° C. After removal of the crystals which formed, the remaining mother liquor was concentrated under reduced pressure until about 50% of the amount remained and, after cooling, a 2nd fraction of crystals resulted. In total, after drying, 66.4 g of colorless crystals were obtained with a creatine content of 89.0% and a residual water content of 11%, equivalent to an isolated yield of 58%. The creatine content in the mother liquor was 1.3%, and thus the calculated yield from the reaction was 68%.

EXAMPLE 2

Reaction of sarcosine sodium salt solution with calcium cyanamide at pH 11 in the presence of sulfuric acid The reaction was carried out as in Example 1 with the exception of the pH (pH 11 in place of pH 10) and afforded a total yield of creatine of 56%.

EXAMPLE 3

Reaction of Sarcosine Sodium Salt Solution with Calcium Cyanamide at pH 10 in the Presence of Phosphoric Acid The reaction was carried out as in Example 1. The pH was adjusted using 85% strength phosphoric acid. Creatine was obtained in a total yield of 75% with a purity before recrystallization of about 89%.

EXAMPLE 4

Reaction of Sarcosine Sodium Salt Solution with Calcium Cyanamide at pH 10 in the Presence of a Mixture of Sulfuric Acid and Phosphoric Acid The reaction was carried out as in Example 1 using a mixture of sulfuric acid and phosphoric acid in place of sulfuric acid to adjust the pH. Creatine was obtained in a total yield of 86% with a purity before recrystallization of about 95%.

We claim:

1. A process for preparing substituted guanidine derivatives of the formula I,

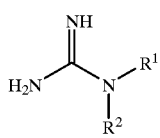
I which comprises reacting calcium cyanamide with a primary or secondary amino carboxylic acid or a primary or secondary amino sulfonic acid or derivatives thereof, of the formula II

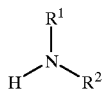
II where the substituents $R^1$ and $R^2$ have, independently of one another, the following meanings:

$R^1$    H,
         $C_1$—$C_{20}$-alkyl;
$R^2$    —($C_1$—$C_{20}$-alkylene)—$COOR^3$,
         —($C_1$—$C_{20}$-alkylene)—$CONR^4R^5$, —($C_1$—$C_{20}$-alkylene)—CN,
         —($C_1$—$C_{20}$-alkylene)—$SO_2R^6$;
$R^3$    H, $C_1$—$C_{20}$-alkyl, $C_2$—$C_{10}$-alkenyl, $C_3$—$C_8$-cycloalkyl,
         $C_6$—$C_{18}$-aryl,
         Na, K, Li, Ca, Mg, $N(R^1)_4$;
$R^4$ and $R^5$ independently of one another
         H, $C_1$—$C_{20}$-alkyl, $C_2$—$C_{10}$-alkenyl, $C_3$—$C_8$-cycloalkyl,
         $C_6$—$C_{18}$-aryl;
$R^6$    $OR^7$, $N(R^8)_2$;
$R^7$    H, $C_1$—$C_{20}$-alkyl, $C_2$—$C_{10}$-alkenyl, $C_3$—$C_8$-cycloalkyl,
         $C_6$—$C_{18}$-aryl,
         Na, K, Li, Ca, Mg, $N(R^1)_4$;
$R^8$    H, $C_1$—$C_{20}$-alkyl, $C_2$—$C_{10}$-alkenyl, $C_3$—$C_8$-cycloalkyl,
         $C_6$—$C_{18}$-aryl.

2. The process as claimed in claim 1, wherein calcium cyanamide is reacted with a primary or secondary amine of the formula II in water and/or a water-miscible organic solvent at from 20 to 120° C. and at a pH of from 6 to 14.

3. The process as claimed in claim 1, wherein said calcium cyanamide is technical grade nitrolime having a calcium cyanamide content of from 30 to 95% by weight.

4. The process as claimed in claim 1, wherein the amino carboxylic acid or amino sulfonic acid or derivatives thereof is/are soluble in water or in a water-miscible solvent.

5. The process as claimed in claim 4, wherein said amino carboxylic acid is sarcosine.

6. A process for preparing substituted guanidine derivatives of formula I:

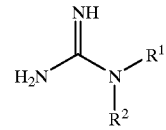
I which comprises reacting nitrolime with a primary or secondary carboxylic acid or a primary or secondary amino sulfonic acid or derivatives thereof of formula II:

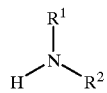
II wherein substituents $R^1$ and $R^2$, independently of each other, have the following meanings:

$R^3$    H, $C_1$—$C_{20}$-alkyl,
         $C_2$—$C_{10}$-alkenyl, $C_3$—$C_8$-cycloalkyl, $C_6$—$C_{18}$-aryl, Na, K,
         Li, Ca, Mg, $N(R^1)_4$;
$R^4$ and $R^5$ independently of one another
         H, $C_1$—$C_{20}$-alkyl,
         $C_2$—$C_{10}$-alkenyl, $C_3$—$C_8$-cycloalkyl, $C_6$—$C_{18}$-aryl,
         $C_6$—$C_{18}$-aryl;
$R^6$    $OR^7$, $N(R^8)_2$;
$R^7$    H, $C_1$—$C_{20}$-alkyl, $C_2$—$C_{20}$-alkenyl, $C_3$—$C_8$-cycloalkyl,
         $C_6$—$C_{18}$-aryl; Na, K, Li, Ca, Mg, $N(R^1)_4$;
$R^8$    H, $C_1$—$C_{20}$-alkyl,
         $C_2$—$C_{10}$-alkenyl, $C_3$—$C_8$-cycloalkyl, $C_6$—$C_{18}$-aryl.

7. The process of claim 6, wherein said nitrolime contains from 5 to 98% by weight CaNCN and is a reaction product of $CaC_2$ and $N_2$ at 800–1100° C.

8. The process of claim 7, wherein the amount of CaNCN in said nitrolime ranges from 20 to 95% by weight.

9. The process of claim 7, wherein said amount of CaNCN in said nitrolime ranges from 30 to 90% by weight.

10. The process of claim 6, wherein the reaction occurs at a pH of 6 to 14 and a temperature of 20 to 120° C.

11. The process of claim 10, wherein said pH ranges from 8 to 12.

12. The process of claim 11, wherein said pH ranges from 9 to 11.

13. The process of claim 10, wherein said temperature ranges from 40 to 80° C.

14. The process of claim 1, wherein the molar ratio of calcium cyanamide to primary or secondary amino carboxylic acid or primary or secondary amino sulfonic acid or derivatives thereof ranges from 0.9 to 5.0.

15. The process of claim 14, wherein said molar ratio ranges from 0.9 to 4.0.

* * * * *